United States Patent [19]
von Nehring et al.

[11] Patent Number: 5,156,194
[45] Date of Patent: Oct. 20, 1992

[54] NET WEIGHT DISPENSING SYSTEM AND METHOD

[75] Inventors: Q. Gordon von Nehring; John O. Beyer, both of Midland, Mich.

[73] Assignee: The Dow Chemical Company, Midland, Mich.

[21] Appl. No.: 604,915

[22] Filed: Oct. 26, 1990

[51] Int. Cl.$^5$ .............................................. B65B 3/28
[52] U.S. Cl. ........................................ 141/1; 141/83; 177/70
[58] Field of Search .................... 141/1, 4, 5, 9, 83, 141/94, 102, 104; 177/70; 364/502, 509, 567

[56] References Cited

U.S. PATENT DOCUMENTS

| | | | |
|---|---|---|---|
| 3,101,801 | 8/1963 | Miller | 177/70 |
| 3,425,501 | 2/1969 | Ganko | 177/70 |
| 4,272,824 | 6/1981 | Lewinger | 141/83 X |
| 4,350,186 | 9/1982 | Schalkowsky et al. | 141/83 |
| 4,469,146 | 9/1984 | Campball et al. | 177/70 X |

FOREIGN PATENT DOCUMENTS 1584639 2/1981 United Kingdom .................. 177/70

Primary Examiner—William A. Cuchlinski, Jr.
Assistant Examiner—G. Bradley Bennett

[57] ABSTRACT

A method and system for dispensing a fluid to provide a predetermined weight percent concentration of a sample material to the fluid. An estimated density value for the fluid is used to determine the volume of fluid to dispense in an initial injection of fluid which is less than the total volume of fluid required to achieve the predetermined weight percent concentration. A working fluid density is then determined from the volume of fluid dispensed and a measurement of the weight of the fluid dispensed. The working density is then used to determine the volume of fluid to dispense in a subsequent injection. Preferably, at least three fluid injections are performed, and the working density is determined after each fluid injection.

30 Claims, 3 Drawing Sheets

NET WEIGHT DISPENSING SYSTEM AND METHOD

MICROFICHE APPENDIX

This specification includes a microfiches appendix having one microfiche with 52 frames.

BACKGROUND OF THE INVENTION

The present invention relates generally to the preparation of mixtures and solutions, and particularly to a system which is capable of repeatably dispensing a very precise weight percent concentration of a fluid to a selected material.

Analytical grade solutions are typically prepared by skilled technicians using a manually implemented procedure. This procedure generally begins by adding the sample material or analytical standard material to a container until the weight of the material is within a prestated acceptable weight range. Then, the material is diluted with a solvent until a constant volume is reached. As a result, the solution concentration will vary within the weight variation of the sample/standard material, and there may also be some variability due to the volume of solvent added. While the incorporation of an internal standard in the solvent may adjust for the volume uncertainty, additional variability may nonetheless exist due to variations in the solvent or internal standard solution weight with temperature.

This procedure may be automated by a robot system, such as that available from Zymark Corporation, Zymark Center, Hopkinton, MA 01748. This type of robotic system is capable of weighing the amount of liquid solvent added as part of the sample preparation. However, no control of the ratio of the sample to solvent weight is provided. Additionally, the manner of adding the sample slowly (e.g., by gently tapping the container) is relatively slow and may expose the sample to the atmosphere for a lengthy time. Such exposure could lead to possible moisture or decomposition concerns with some sample materials (e.g., the loss of volatile components). Additionally, the presence of vibrations (e.g., from tapping) is known to cause particle size discrimination which could lead to non-representative sampling of non-homogeneous materials.

Another approach to preparing analytical solutions is represented by the Stanprep dispenser manufactured by Spiral Systems, Inc., Cincinnati, Ohio. A description of this type of dispenser is presented in Campbell et. al. U.S. Pat. No. 4,469,146, issued on Sep. 4, 1984, and entitled "Apparatus And Process For Preparing Quantitative Chemical Solutions". This dispenser apparatus utilizes a table of solution densities to estimate the weight amount of liquid solvent to add. This amount of solvent is then added and weighed. If the weight is under that estimated, then a correction is made by adding more solvent until the initially calculated solvent plus solute weight is reached. However, if the weight is over that initially estimated, then the apparatus responds with an error indicator. Additionally, since densities are not constant, there may be some concentration variability with this apparatus due to density shifts with temperature. This apparatus also requires extensive density tables to be created, either by estimation or by empirical measurement.

Accordingly, it is a principal objective of the present invention to provide a rapid and automatic method and system for dispensing a series of fluid volumes to repeatably create mixtures or solutions having a very precise weight percent concentration.

It is a more specific objective of the present invention to provide a net weight dispensing method and system which controls the final weight percent concentration, rather than attempting to hold volume or weight to an arbitrary tolerance.

It is an additional objective of the present invention to provide a net weight dispensing method and system which may be operated with only a minimal amount of training.

It is a further objective of the present invention to provide a net weight dispensing method and system which is not sensitive to density variations when solutions are prepared at different times or under different conditions.

It is another objective of the present invention to provide a net weight dispensing method and system which is capable of self-calibration in connection with each dispensing operation.

SUMMARY OF THE PRESENT INVENTION

In order to the achieve the foregoing objectives, the present invention provides a method of preparing a mixture or solution in which a target weight of fluid/solvent is first determined in response to the measurement of the weight of a sample/solute which has been introduced into a container vessel. A target volume of solvent to add to the container is then determined from a combination of the target weight of the solvent and an estimate of the density of the solvent. A predetermined portion of the target volume of the solvent is then added to the container. This predetermined portion is less than the total target volume of the solvent. The container is then reweighed with the solute and solvent residing therein. Thereafter, the density of the solvent is determined in response to the weight measurement of the solvent volume added to the container. The additional volume of solvent needed to be added to the container in order to substantially achieve the target weight of the solvent is then determined. At least one additional volume of solvent is then added to the container to achieve the target weight. Preferably, the additional volume of solvent is dispensed to the container in a predetermined sequence of at least two injections. This sequence also permits a redetermination of the solvent density after each solvent injection.

The system of the present invention includes an analytical balance for measuring the weight of a quantity of a sample material introduced into a container and the weight of selected solvent volumes subsequently added to the container. The analytical balance then produces an output signal which is indicative of the weight being measured. A volumetric dispenser is also provided for injecting selected volumes of the solvent into the container. An input device, such as a computer keyboard, is used for identifying a density characteristic of the solvent. The input device is also used for identifying the predetermined weight percent concentration ratio of the solute and the solvent in the final mixture or solution. The system also includes a computer controller which is operatively connected to the analytical balance, the input device and the volumetric dispenser. The computer controller is programmed to cause the dispenser to add selected volumes of the solvent to the container in order to substantially achieve the predetermined weight percent concentration in accordance with the programmed sequence of measurements and solvent injections.

With this arrangement, interactions with the system may be prompted by the transmission of messages from the computer controller to a display device associated with the computer. A printer may also be provided to generate a report identifying such information as the date, time, analyst, sample name, sample weight, total solvent weight, and any other additional relevant information.

One of the important advantages of the present invention is the accuracy which may be repeatedly attained under differing conditions. In this regard, the present invention is capable of achieving an actual weight which will agree within approximately 0.01 percent (relative standard deviation) of the target weight. Indeed, even this minute uncertainty is only limited by the accuracy of the balance used to weigh the solute and solvent materials. The predetermined ratio of solute to solvent weight can be reproduced by the system according to the present invention with this high level of precision at any given time.

Additional advantages and features of the present invention may be seen from the description of the drawings.

DETAILED DESCRIPTION OF THE PREFERRED EMBODIMENT

Figure 1:
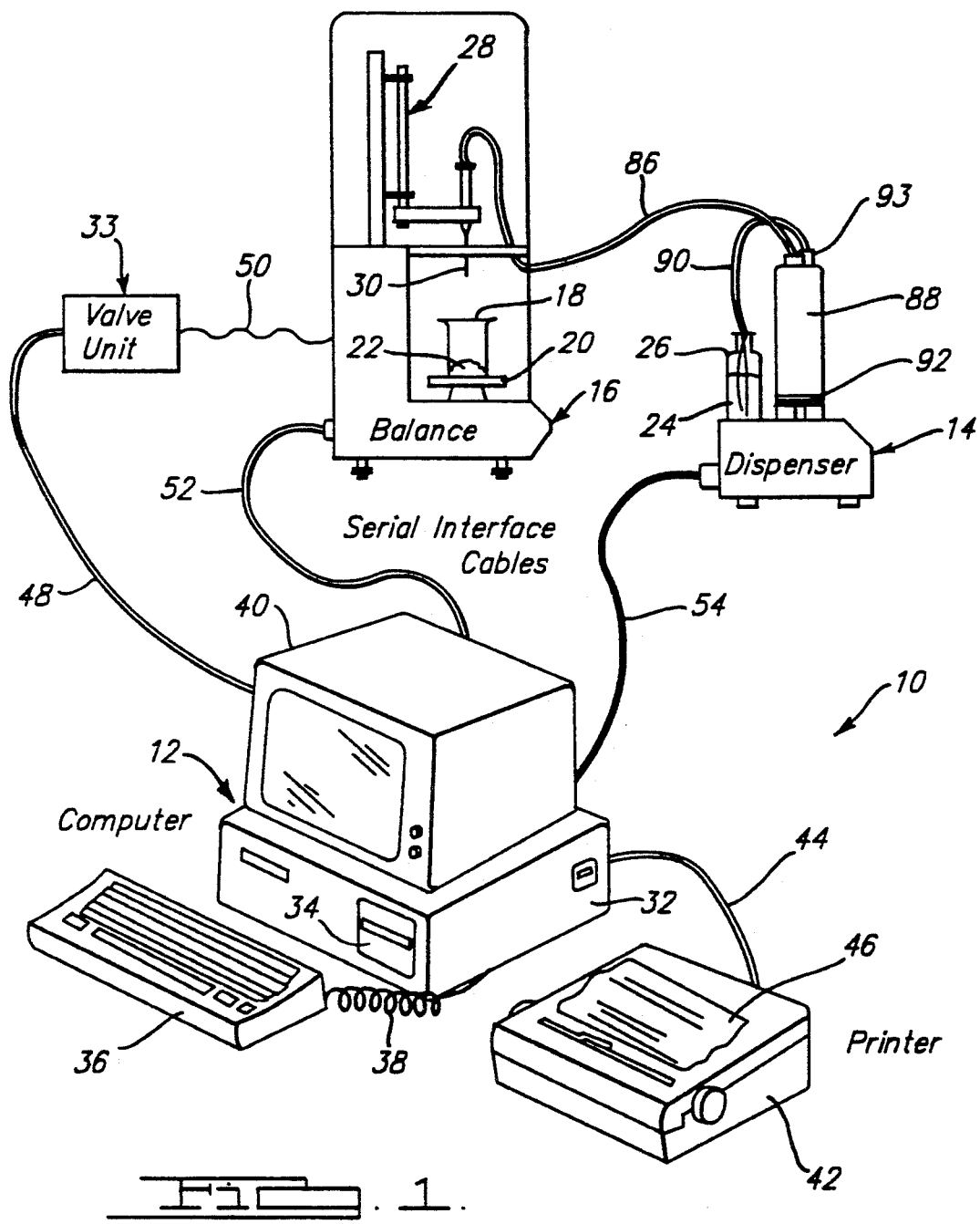
FIG. 1 is a diagrammatic representation of a net weight dispensing system according to the present invention.

Referring to FIG. 1, the net weight dispensing system 10 according to the present invention is shown to generally comprise a computer system 12, a volumetric dispenser 14 and an analytical balance 16. As will be discussed more fully below, the computer system 12 is used to control the operation of the dispenser 14 and the analytical balance 16. FIG. 1 also shows a container or vessel 18 which is disposed on the weighing pan 20 of the analytical balance 16. For illustration purposes, the container 18 is shown to include a quantity of sample material 22 which will represent the solute when a solution is prepared under the method according to the present invention.

As will be more fully described below, the analytical balance 16 is used to measure the weight of the container 18 before the sample material 22 is introduced to the container. Subsequently, a desired quantity of the sample material may be introduced into the container 18 using a scoop, spoon or the like, such as the scoop 23, shown in FIG. 3. In this regard, it is important to understand that the amount of sample material being added to the container 18 need not be precisely determined in advance. The weight of the sample material introduced into the container 18 need only be within a range which will insure that the dispenser delivers an acceptably accurate volume of fluid/solvent to the container.

Whenever a weight measurement is made, it may be appropriate to "tare" the balance 16 to read zero. Thus, once the container 18 is weighed and the measured value transmitted to the computer 12, this value will be stored in the computer, and the computer may then command the balance to zero itself. This provision of taring the balance may be advisable with some types of balances to enhance the accuracy of the next weight measurement.

Once the sample material has been introduced into the container 18, the computer system 12 will instruct the analytical balance 16 to weigh the combination of the container 18 and the sample material 22 disposed therein Since the weight of the container 18 has already been measured and the balance 16 tared, the computer 12 will receive a direct measurement of the sample material weight from the balance. However, if the balance is not tared, the computer controller 12 will subtract the container weight from the total weight measured to determine the sample weight. Assuming that the sample weight is within the acceptable range, the computer 12 will then determine a solvent "target" weight which is necessary to create a mixture or solution having a desired weight ratio of the sample material to the solvent The dispenser 14 is used to dispense selected volumes of a solvent 24 from a source such as reservoir 26. FIG. 1 also shows that the dispenser 14 includes a pneumatically operated assembly 28 for lowering and raising a nozzle 30 of the dispenser 14 into and out of the container 18. In one form of the present invention, the dispenser 14 is comprised of a Dosimat model 665 dispenser from Brinkman Instruments, Westbury, NY. Additionally, the pneumatically operated assembly 28 is generally comprised of a model 028-D 8 in. air piston assembly from Bimba Manufacturing Co., Monee, IL. However, it should be appreciated that other suitable dispensing mechanisms may be employed which are capable of delivering precise volumes of fluid (e.g. 1 part/10,000) under automated control.

The analytical balance 16 may be any suitable balance mechanism which is both appropriate to the weight being measured and the accuracy needed to be achieved. Thus, for example, the analytical balance 16 may be comprised of a model GA160 or GA200 analytical balance (with two way communication board) from Ohaus Corporation, Florham Park, NJ. The computer 12 may be any suitable computer system capable of implementing the method according to the present invention. As one example of an appropriate computer, the computer 12 may be comprised of a Dell System 200 or 286 PC AT-compatible computer from Dell Computer Corporation, Austin, TX., equipped with a math co-processor, a hard disk drive (optional), a color monitor and the necessary parallel and serial interface boards.

In FIG. 1, the computer 12 is shown to include a hardware enclosure 32 which contains the computer's internal mother board, RAM memory card, hard disk drive, video controller card, and its parallel and serial interface boards. In this regard, one example of a suitable interface board is represented by the PIO-12 24-bit parallel digital I/O interface board from Keithley Metrabyte/ASYST/DAC, Taunton, MA. This board may be used to control a contact closure interface unit 33, which will be discussed below.

FIG. 1 also shows that the computer also includes a floppy disk drive 34, which may be used in addition to or in lieu of the computer's hard disk drive. Thus, for example, the computer program, described generally in connection with FIG. 4 below, could be contained on either the floppy disk drive 34 or the hard disk drive (if available). Similarly, files set up to perform specific dispensing operations according to the present invention could be stored on either the floppy disk drive 34 or the hard disk drive (if available).

FIG. 1 also shows that the computer 12 is provided with a keyboard 36, which is used to enter information, such as the information needed by the computer to create specific files for dispensing a predetermined percent weight concentration of a particular solvent with a particular solute. The keyboard 36 is connected to the computer via cable 38. While not actually required to perform an actual dispensing operation, the computer 12 is also shown to include a color monitor 40. The color monitor 40 assists the interaction of the analyst with the computer 12 by displaying the information entered via the keyboard and displaying information generated in response by the computer. The color monitor 40 may also be used to display the results of the dispensing operation which has been performed.

The computer 12 may also transmit the results to a printer 42, which is connected to the computer 12 via cable 44. In one form of the present invention, the printer 42 is an FX-80 parallel printer from Epson America, Inc., Torrance, CA. In this regard, it should be appreciated that any suitable printer may be provided which is capable of generating a hard copy of the results (or other information from the computer 12) on paper 46.

As mentioned above, the computer 12 is provided with a contact closure interface unit 33. The unit 33 is connected to the computer via parallel cable 48. The unit 33 is used to control the air cylinder of the pneumatically operated assembly 28, and pass through signals from the switches on the sliding doors of the analytical balance 16. Accordingly, the interface unit 33 includes one or more solenoid valves to control air pressure to the air cylinder of the assembly 28. In one form of the present invention, the unit 33 includes an Asco 4-port valve from the Automatic Switch Co., Florham Park, NJ, and an optically isolated relay (model 20D3) from Opto22, Huntington Beach, CA. The optically isolated relay is used to electrically isolate the valve from the computer 12. In another form of the present invention, the unit 33 may be comprised of a digital valve interface ("DVI") from Valco Instruments Company, Inc., Houston, TX and an invertor chip (type HEF40098BP) from Philips Electronics—PHIN, Lindhoven, Netherlands. The PIO-12 board identified above is used to read the switches on the sliding doors of the analytical balance 16, as will be discussed further below. Accordingly, a plurality of air and electric signal lines 50 are used to connect the unit 33 with the pneumatically operated assembly 28 and the door switches.

FIG. 1 also shows that an RS-232 serial cable 52 is connected between the computer 12 and the analytical balance 16 to provide two-way communication between the computer and the analytical balance 16. Similarly, another RS-232 serial cable 54 is connected between the computer 12 and the dispenser 16 to provide two-way communication from the computer and the dispenser.

Figure 2:
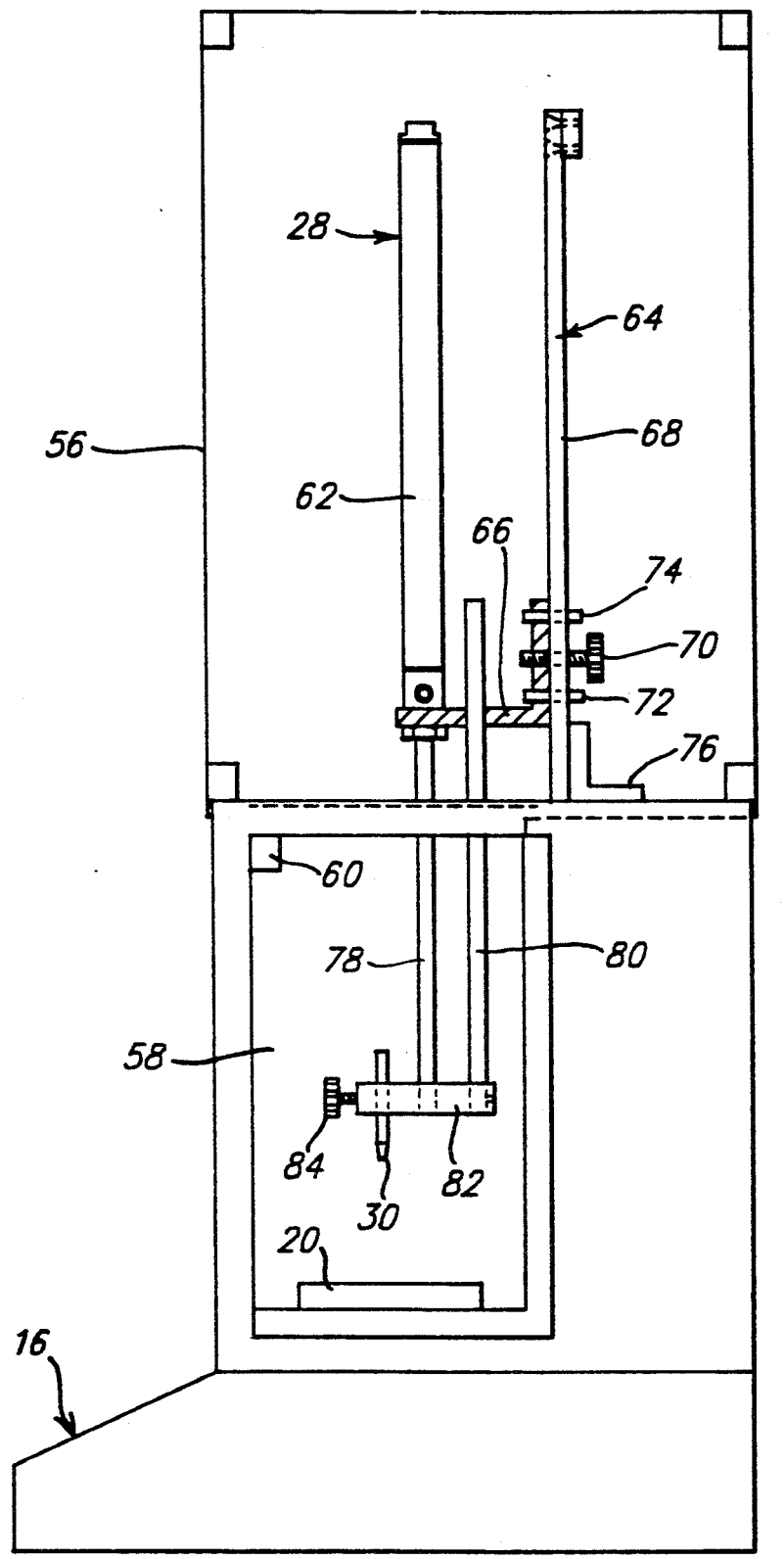
FIG. 2 is a diagrammatic side elevation view of the balance and the pneumatically operated assembly shown in FIG. 1.

Referring to FIG. 2, a diagrammatic side elevation view of the analytical balance 16 and pneumatically operated assembly 28 is shown. In this regard, it should be appreciated that it is desirable to avoid any air drafts through the balance which could affect the accuracy of the measurements being made. Accordingly, FIG. 2 shows the provision for a transparent enclosure 56 which is adapted to sit on top of the analytical balance 16. The five-sided enclosure 56 may be constructed of any suitable material, such as Lexan panels (a General Electric trademark). The analytical balance 16 is also provided with one or more sliding doors 58 which are used to provide access to the weighing pan 20. While these doors 58 should be closed whenever a measurement is being made, the system 10 preferably also includes a switch mechanism 60 which is capable of detecting whether or not the doors are closed. In this way, a message may be displayed on the monitor 40 which will prompt the analyst to close the balance doors should the system detect that the doors are not fully closed. In one form of the present invention, the switch 60 is a Honeywell micro-switch (11SX21-T) and lever (JX40) mechanism which is mounted to the balance to permit the door to engage the lever of the switch mechanism when the door is fully closed.

FIG. 2 also shows that the pneumatically operated assembly 28 generally comprises an air cylinder 62 which is supported on a guide way structure 64. Specifically, the air cylinder 62 is mounted to an "L" shaped bracket 66 of the guide way structure 64, such that the air cylinder extends in a generally vertical direction. The bracket 66 is movably mounted to a guide way plate via locking screw 70 and guide pins 72-74. In this regard, the guide way plate includes a vertically extending slot which permits the bracket 66 to be raised or lowered to a desirable position Another "L" shaped bracket 76 is used to secure the guide way plate 68 to the top of the balance 16 by any suitable means, such as a plurality of bolts.

As shown in FIG. 2, the air cylinder 62 includes a piston rod 78 (shown in a fully extended position). In this regard, it should be appreciated that the piston rod 78 extends and retracts under computer control via command signals transmitted to the solenoid valve in the interface unit 33. An anti-rotating guide rod 80 and a retainer plate 82 are also provided to stabilize the travel of the piston rod 78 and hold nozzle or tip 30 of the dispenser 14. Specifically, the horizontally disposed retainer plate 82 is mounted to one end of the piston rod 78 and to one end of the guide rod 80, such that these two rods extend generally in parallel to each other. The guide rod 80 also extends through a hole in the bracket 66 to permit vertical sliding movement of the guide rod relative to the bracket 66. A locking screw 84 is also connected to the retainer plate 82 by a threaded engagement to permit the nozzle 30 to be removably secured to the retainer plate.

Accordingly, it should be appreciated that the assembly 28 is constructed to enable the nozzle 30 to be lowered either into or sufficiently near to the container 18, so that fluid may be dispensed to the container through conduit 86 (shown in FIG. 1) without causing any fluid to splash outside of the container. In this regard, FIG. 1 also shows that the dispenser 14 includes a cylinder 88 which is connected to the reservoir 26 via conduit 90. The cylinder 88 includes a piston 92 which is used to draw fluid from the reservoir 26 on a down stroke and inject selected volumes of this fluid into the container 18 via conduit 86 on an upstroke. The cylinder 88 is also equipped with a three port valve, generally designated by reference numeral 93, for controlling fluid flow through conduits 86 and 90.

In order to assure maximum accuracy, it is preferred that all of the fluid volume required to meet the predetermined weight percent concentration be loaded into the cylinder 88 prior to any fluid injections into the container 18. However, where this is not possible, then the volume of the first injection should be large enough to require that the necessary refill stroke(s) of the piston 92 be made during this injection. This procedure will permit all of the subsequent injections to be made without having to refill the cylinder 88. In this way, any volumetric error introduced by the refill stroke, such as caused by the presence of an air bubble, will be limited to the first injection. Thereafter, the subsequent injections may be more potentially precise, and the density value achieved for the fluid in these injections may be more accurate.

Figure 3:
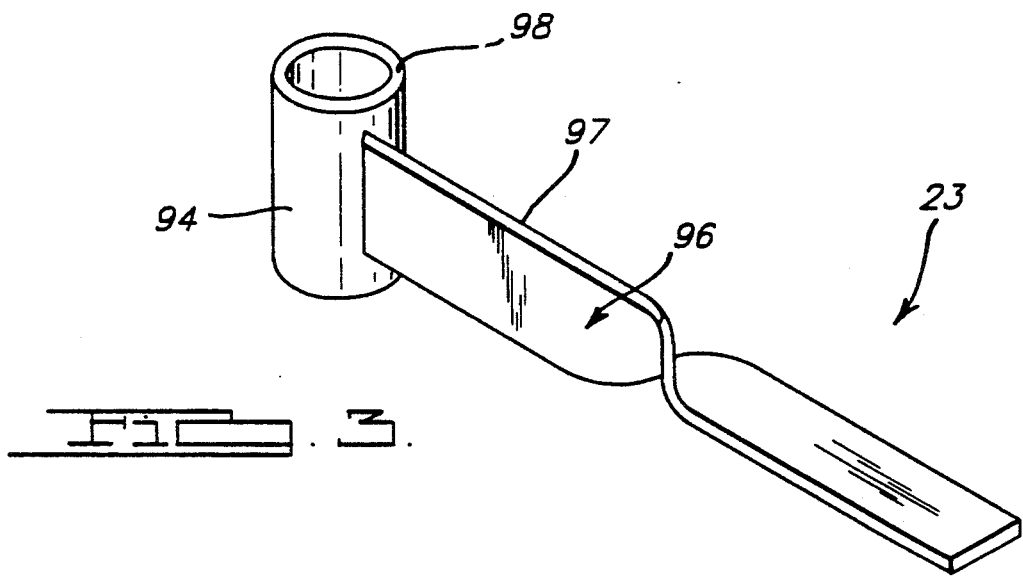
FIG. 3 is a perspective view of a scoop which may be used to introduce sample material into the container shown in FIG. 1.

Referring to FIG. 3, a perspective view is shown of a scoop 23 that may be used to add sample material to the container 18. In this regard, the scoop 23 is designed to make it easier provide a reliable amount of material to the container 18. The scoop 23 is comprised of a cup 94 and a handle 96 which extends laterally from the cylindrical side thereof. The size of the cup 94 is preferably constructed to provide an amount of sample material which is in the middle of the acceptable sample material weight range. The cup 94 includes a relatively narrow opening 98 which will help to avoid spilling the material as the scoop is moved into the balance 16. Additionally, the handle 96 is formed with a ninety degree twist and a knife edge 97, which will help to avoid sample material particles from accumulating on the portion of the handle closest to the cup 94. When the sample material is a fluid, any suitable transfer device, such as an eyedropper, may be used to introduce the fluid into the container.

Figure 4:
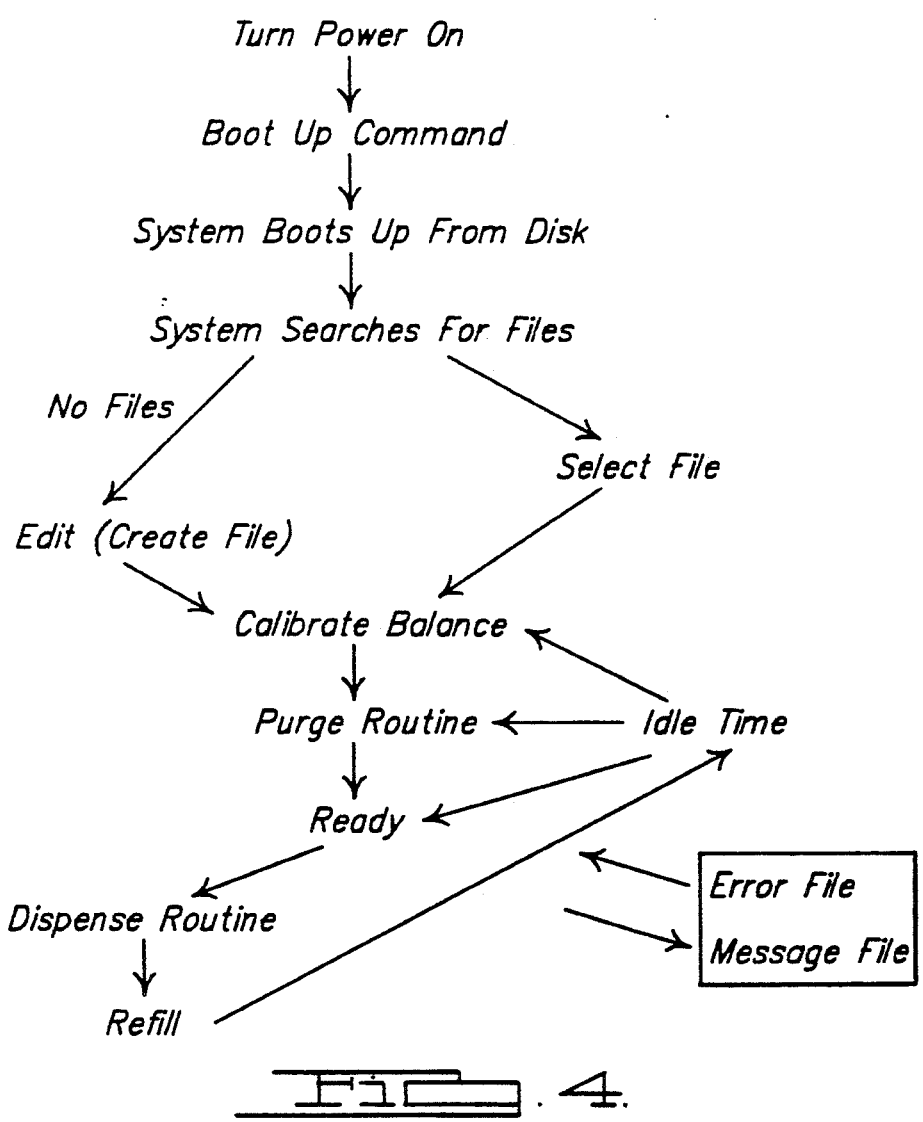
FIG. 4 is an overall flowchart of the computer program included herein as a microfiche appendix.

Referring to FIG. 4, an overall flowchart is shown for the computer program included herewith as a microfiche appendix. In this regard, FIG. 4 indicates that analyst will command the computer to boot up the computer program from the appropriate disk drive of the computer 12 after the power is turned on. Then, the analyst is able to choose whether an existing file should be selected or whether a new file should be created in an "Edit" mode. In this regard, the table below sets forth one example of a file as structured by the computer program.

| File Date | |
|---|---|
| File Number: | 5 |
| File Name: | BCK453EE.DBF |
| Balance Calibration Weight: | 50 ± .0001 Gm |
| Balance Calibration Interval: | 24 Hours |
| Container Weight & Tolerance: | 51.0 ± 5.0 Gm |
| Target Sample Weight & Tolerance: | 0.400 ± 0.100 Gm |
| Target Solvent Weight & Tol. (SW): | 12.8134 ± 3.21 Gm |
| Target Ratio of (SA) to (SW) & Tol.: | 0.031217319 ± 0.000300 Gm |
| Ratio of Internal Standard/ Solution: | 0.012824081 ± 0.00020 Gm |
| Density & Tolerance at 70 Degree F.: | 0.780 ± 0.015 Gm |
| Dispenser Syringe Size: | 50 |
| Idle Time Before Solvent Purge: | 0.50 Hours |
| Solvent Purge Volume (mL): | 10 |
| % of Solvent to Add at Steps: | 50% & 90% & 10% |

-continued

| File Date | |
|---|---|
| Instructions | |

As shown in this table, each file is preferably assigned a file number and a file name. Then, the "Balance Calibration Weight" refers to a quantity in terms of weight (in grams) entered by the analyst using the keyboard 36. This calibration weight is used in the "Calibrate Balance" routine identified in FIG. 4. In this regard, the balance 16 may be conveniently calibrated by using a certified standard weight with a known weight of 50 grams. If the weight of this standard weight falls outside of the range indicated, then the system 10 determines that the balance needs to be re-calibrated before continuing its operation. Additionally, it should be noted that the time interval of this calibration routine may be selected, and in the example illustrated, this interval is every 24 hours.

As noted in the table, the file also includes an entry for the "Container Weight & Tolerance". In the specific example, the Container Weight is listed as 51 grams. Once the system is in its "Dispense Routine" identified in FIG. 4, the weight the container 18 must be within the container weight and tolerance specified in order for the dispensing operation to continue.

As listed in the table, each of the weights listed in the file are also specified with an analyst-selected tolerance range (e.g., grams, milligrams, or %). These tolerance ranges provide a self check of the system operation to insure overall accuracy and effectiveness. For example, the "Target Sample Weight & Tolerance (SW)" provides a relatively broad range of sample weights within which the system will operate with maximum accuracy. In other words, the analyst need not precisely add a very specific amount of sample (via scoop 23) to the container in order for the system to proceed to the next step. Rather, the sample weight tolerance may be set to avoid the need for a refill stroke of the dispenser piston 92, or avoid the possibility of dispensing more fluid than the container is capable of holding.

The "Target Ratio of (SA) to (SW) & Tolerance" entry refers to the specific weight percent concentration of sample material/solute to fluid/solvent that is desired by the analyst, expressed as the ratio of sample material/solute weight to fluid/solvent weight. As indicated by the example set forth in the table, the system 10 is capable of achieving a very accurate and precise weight percent concentration. Additionally, should the actual weight percent concentration measured by the system exceed the selected tolerance level, then the system will generate an appropriate message to this effect on either or both of the monitor 40 and the printer 42.

The "Ratio of Internal Standard / Solution" entry in the table refers to the fact that the fluid 24 in the reservoir 26 may include a calibration marker as an internal standard, and that weight of the fluid added should provide a specific ratio of internal standard weight to sample weight when the operation is completed. The "Density & Tolerance at 70 Degree F" entry in the table refers to the initial density value for the fluid. The final working density determined from the last dispensing operation is stored for future use as the working density. In this regard, it should be understood that system requires an initial density value and tolerance range to be entered. However, as the dispensing operation proceeds, a working density will be determined after each fluid injection (i.e., weight measured/volume dispensed). The final working density will automatically be stored in the file as the operation is completed in addition to the initial estimated density value. This aspect of the present invention is particularly advantageous when successive dispensing operations are to be performed, as the final working density from the immediately prior dispensing operation will permit a more accurate initial fluid injection to be made in the next dispensing operation.

The "Dispenser Syringe Size" entry in the table is useful for permitting the system to determine the maximum volume of fluid which may be dispensed from a single stroke of the piston 92 of the dispenser 14. The "Idle Time Before Solvent Purge" entry refers to the time that the system will permit between dispensing operations before the analyst will be instructed to execute the "Solvent Purge Volume" routine listed, before any further dispensing operations are permitted. This aspect of the present invention is referred to in FIG. 4 as the "Purge Routine", and it serves to avoid the possibility of the nozzle 30 becoming plugged with internal standard during Idle Times (due to evaporation of the solvent) and to avoid errors in the volume of solvent delivered in the first addition (due to solvent evaporation).

The table also includes an entry labeled "% of Solvent to Add at Steps", and the specific example given is "50%, 90%, and 10%". Each of these percent values refer to the weight of individual fluid volumes to be dispensed or injected into the container 18. As indicated above, the system 10 preferably provides for at least three successive fluid injections, and the analyst may control the weight percent of each fluid injection as a function of the total fluid weight require to reach the predetermined weight percent concentration specified above. For example, in this particular instance, the dispenser will be instructed to add a fluid volume in the first injection which will provide approximately 50% of the total fluid weight required to meet the Target Solvent Weight. Similarly, the second injection will provide a fluid volume which will add the fluid/solvent weight in the container to approximately 90% of the residual Target Solvent Weight. Finally, the third injection will provide the remaining fluid volume to reach the Target Solvent Weight. It should be appreciated that these percent values are only approximated as the density of the fluid at the time may vary from either the initial density value entered or the final working density value from the last dispensing operation.

In light of the variability of the density value, it is preferred that the percent value for the initial injection provide sufficient fluid volume that an accurate density value may be determined by the computer 12 from the volume of fluid dispensed and the weight measured by the balance 16. The percent value for the second injection should be selected in a similar manner, and it should also be such as to bring the fluid weight transferred close to the Target Solvent Weight After this second injection, the computer will again update the density value for the fluid, and this value may be more reliable as any air bubbles should have been purged from the system during the first injection. After the third or last injection, the computer 12 will determine a final density value, which is preferably stored in the file as the density value to be used for the next dispensing operation.

This programmed process of measuring weight and sequentially injecting selected volumes of fluid is identified in FIG. 4 as the "Dispense Routine". The final step of the program labeled "Refill" refers to fact that the dispenser 14 is preferably re-indexed after each dispensing operation in order to be ready for the next dispensing operation. The "Error File" and "Message File" box in FIG. 4 refers to the ability of the system 10 to generate informative messages and messages which will prompt action by the analyst. For example, the error messages may include a message indicating that the container weight is out of tolerance, and a message that there is an inability to communicate with an external device, such as the dispenser 14. The computer program for the system 10 is also designed to cause the printer 42 to produce a paper copy of the dispenser operation, such as an indication of the container weight, the sample weight, the total solvent weight, and the internal standard marker (if any).

While the system 10 has been described in terms of a single dispenser 14, it should be appreciated that one or more dispensing mechanisms may be employed to inject a plurality of different fluids or slurries into a container. Similarly, the system 10 could also be modified to enable the analyst to introduce two different sample materials into the container. Additionally, it should be appreciated that the sample material may be any material (e.g., solid or liquid) in any suitable form (e.g., particles, tablet or block).

It will be appreciated that the above disclosed embodiment is well calculated to achieve the aforementioned objects of the present invention. In addition, it is evident that those skilled in the art, once given the benefit of the foregoing disclosure, may now make modification of the specific embodiments described herein without departing from the spirit of the present invention. Such modifications are to be considered within the scope of the present invention which is limited solely by the scope and spirit of the appended claims.

We claim:

1. A method of dispensing a fluid to provide a predetermined weight percent concentration of said fluid relative to a sample material, comprising the steps of:
   weighing a vessel;
   introducing a quantity of said sample material into said vessel and reweighing said vessel with said sample material contained therein;
   determining a target weight of said fluid in response to the weight of said sample material, and determining a target volume of said fluid to add to said vessel from the combination of said target weight and an initial density value of said fluid;
   dispensing a predetermined portion of said target volume of said fluid to said vessel which is less than said target volume, and reweighing said vessel with said sample material and fluid contained therein;
   determining a working density of said fluid in response to said second reweighing step, and determining a volume of fluid to be added to said vessel from said working density in order to substantially achieve said target weight of said fluid; and
   dispensing at least one additional volume of said fluid to said vessel to substantially achieve said target weight of said fluid.

2. The method according to claim 1, wherein at least two additional volumes of said fluid are dispensed to said vessel after said predetermined portion of said target volume of said fluid has been dispensed in order to substantially achieve said target weight of said fluid.

3. The method according to claim 2, wherein the weight of said fluid dispensed to said vessel is measured after each of said fluid dispensing steps.

4. The method according to claim 3, including the step of redetermining the working density of said fluid prior to the step of dispensing the last additional volume of said fluid to said vessel.

5. The method according to claim 4, further including the step of determining a final working density of said fluid in response to the step of dispensing the last additional volume of said fluid to said vessel, and storing said final working density value for use as the initial density value in a subsequent dispensing procedure.

6. The method according to claim 1, wherein a balance is used to perform said weighing steps, and said balance is tared after each weighing step to zero said balance.

7. The method according to claim 6, including the step of determining whether said balance is protected from air drafts prior to said step of weighing said vessel.

8. The method according to claim 1, wherein said fluid is a solvent for said sample material.

9. The method according to claim 1, including the step of determining whether the weight of said sample material introduced into said vessel is within a predetermined acceptable weight range.

10. The method according to claim 2, wherein said predetermined portion of said target volume of said fluid represents at least 30 percent of said target volume, and said second dispensing step adds generally between 80 and 95 percent of the remaining fluid volume necessary to substantially achieve said target weight of fluid.

11. A system for dispensing a fluid to provide a predetermined weight percent concentration of a sample material said fluid, comprising
balance means for measuring the weight of a quantity of said sample material introduced into a vessel and the weight of selected fluid volumes subsequently added to said vessel, and for producing a signal indicative of the weight being measured;
dispensing means for delivering selected volumes of said fluid to said vessel;
input means for identifying a density characteristic of said fluid, and for identifying said predetermined weight percent concentration of said sample material in said fluid;
controller means, operatively connected to said balance means, said input means and said dispensing means, for causing said dispensing means to add selected volumes of said fluid to said container to substantially achieve said predetermined weight percent concentration in a programmed sequence of fluid injections of variable volume in which the density of said fluid is determined after at least one of said fluid injections.

12. The system according to claim 11, wherein said controller means includes means for determining the density of said fluid after each of said fluid injections.

13. The system according to claim 12, wherein said programmed sequence provides for at least three fluid injections.

14. The system according to claim 11, wherein said programmed sequence includes a determination of whether the weight of said sample material introduced into said vessel is within a predetermined weight range before any fluid injections are performed.

15. The system according to claim 11, wherein said system includes means for producing a record indicative of weight from the signals received from said balance means.

16. The system according to claim 11, wherein said controller means includes means for storing the signals received from said balance means and said input means.

17. A method of dispensing a fluid to provide a predetermined weight percent concentration of said fluid relative to a sample material, comprising the steps of:
weighing a vessel;
introducing a quantity of said sample material into said vessel and reweighing said vessel with said sample material contained therein;
determining a target weight of said fluid in response to the weight of said sample material, and determining an initial volume of said fluid to add to said vessel from a predetermined portion of said target weight of said fluid and an initial density value of said fluid, said predetermined portion of said target weight of said fluid being less than said target weight;
dispensing said initial volume of said fluid to said vessel, and reweighing said vessel with said sample material and fluid contained therein;
determining a working density of said fluid in response to said second reweighing step, and determining at least one additional volume of fluid to add to said vessel from said working density in order to substantially achieve said target weight of said fluid; and
dispensing said additional volume of said fluid to said vessel.

18. The method according to claim 17, wherein at least two additional volumes of said fluid are dispensed to said vessel after said initial volume of said fluid is dispensed to said vessel in order to substantially achieve said target weight of said fluid.

19. The method according to claim 18, wherein said predetermined portion of said target weight of said fluid represents at least 30 percent of said target weight, and said second dispensing step adds generally between 80 and 95 percent of the remaining fluid weight necessary to substantially achieve said target weight of fluid.

20. A method of preparing an admixture of materials of predetermined concentration; the method comprising:
(a) weighing a first material of the admixture;
(b) calculating the target weight of a second material of the admixture which when admixed with the first material would achieve the desired predetermined concentration;
(c) converting a portion of the calculated target weight to a corresponding volume based on an initial density of the second material, and dispensing the corresponding volume of the second material;
(d) determining the weight of the dispensed second material;
(e) calculating the density of the second material based on the volume of the second material determined in step (c) and the weight of the second material determined in step (d);
(f) calculating the residual weight of the second material necessary to reach the target weight;
(g) converting at least a portion or all of the residual weight to a corresponding residual volume using the calculated density of step (d) and dispensing the residual volume of the second material;

(h) admixing the materials to prepare said admixture of materials of predetermined concentrations.

21. The method of claim 20, wherein one of the materials is a fluid.

22. The method of claim 21, wherein the second material is a liquid.

23. The method of claim 20, wherein steps (e)–(g) are repeated at least once to produce at least a second residual, second calculated density, and second corresponding residual volume, and dispensing the at least second corresponding residual volume of the second material to prepare the admixture.

24. The method of claim 23 wherein the number of repetitions of steps (e)–(g) is predetermined.

25. The method of claim 23 wherein one of the materials is a fluid.

26. The method of claim 24 wherein the second material is a liquid.

27. The method according to claim 23, wherein the portion of said target weight of step (c) represents at least 30 percent of said target weight, said second dispensing step (g) adds generally between 80 and 95 percent of the remaining weight necessary to substantially achieve said target weight of fluid, and at least one repetition of steps (e)–(g) is practiced to achieve said target weight.

28. The method of claim 27 wherein the number of repetitions of steps (e)–(g) is predetermined.

29. The method of claim 28 wherein one of the materials is a fluid.

30. The method of claim 29 wherein the second material is a liquid.

* * * * *